(12) United States Patent
Ahmad et al.

(10) Patent No.: US 10,179,218 B2
(45) Date of Patent: Jan. 15, 2019

(54) DUAL PRESSURE SENSOR CONTINUOUS POSITIVE AIRWAY PRESSURE (CPAP) THERAPY

(75) Inventors: Samir S. Ahmad, San Diego, CA (US); Leonardo Alberto Baloa Welzien, Lake Forest, CA (US); Enrico Brambilla, Irvine, CA (US)

(73) Assignee: BREATHE TECHNOLOGIES, INC., Irvine, CA (US)

( * ) Notice: Subject to any disclaimer, the term of this patent is extended or adjusted under 35 U.S.C. 154(b) by 262 days.

(21) Appl. No.: 13/411,257

(22) Filed: Mar. 2, 2012

(65) Prior Publication Data

US 2013/0228180 A1  Sep. 5, 2013

(51) Int. Cl.
*A61M 16/10* (2006.01)
*A61M 16/00* (2006.01)
*A61M 16/20* (2006.01)

(52) U.S. Cl.
CPC ...... *A61M 16/024* (2017.08); *A61M 16/0051* (2013.01); *A61M 16/0069* (2014.02); *A61M 16/021* (2017.08); *A61M 16/022* (2017.08); *A61M 16/026* (2017.08); *A61M 16/107* (2014.02); *A61M 16/20* (2013.01);
(Continued)

(58) Field of Classification Search
CPC .......... A61M 16/00; A61M 2016/0021; A61M 16/0051; A61M 2230/005; A61M 2016/0069; A61M 2016/0036; A61M 16/0066; A61M 16/0057; A61M 2016/205; A61M 2205/15; A61M 2205/3365;
(Continued)

(56) References Cited

U.S. PATENT DOCUMENTS 4,838,257 A * 6/1989 Hatch ................... A61M 16/00
                                                    128/204.18
5,072,729 A   12/1991 DeVries
(Continued)

FOREIGN PATENT DOCUMENTS

EP         722747 A2    7/1996
WO      2005016217      2/2005
WO      2005016217 A2   2/2005

OTHER PUBLICATIONS

International Search Report and Written Opinion for PCT/2013/28062, dated Apr. 19, 2013.
(Continued)

*Primary Examiner* — Colin W Stuart
*Assistant Examiner* — Douglas Sul
(74) *Attorney, Agent, or Firm* — Stetina Brunda Garred and Brucker; Mark B. Garred (57) ABSTRACT

A continuous positive airway pressure (CPAP) apparatus for respiratory assistance of a pattern is disclosed. There is a blower having an output connectible to a ventilation mask wearable by the patient. A first pressure sensor measures blower pressure at the output of the blower, and a second pressure sensor that is connectible to the ventilation mask measures mask pressure therein. A pressure controller is connected to the first pressure sensor and the second pressure sensor, and a patient inspiratory phase and a patient expiratory phase is be detectable by the pressure controller to regulate therapeutic pressure at the patient mask, based upon pressure differentials between the mask pressure and the blower pressure.

23 Claims, 8 Drawing Sheets

(52) U.S. Cl.
CPC ... *A61M 16/201* (2014.02); *A61M 2016/0021* (2013.01); *A61M 2016/0027* (2013.01); *A61M 2205/18* (2013.01); *A61M 2205/3355* (2013.01); *A61M 2205/3365* (2013.01); *A61M 2205/3368* (2013.01); *A61M 2205/42* (2013.01); *A61M 2205/502* (2013.01)

(58) Field of Classification Search
CPC .. A61M 2205/3331; A61M 2016/0027; A61M 16/021; A61M 16/022; A61M 16/024
USPC ............ 128/204.18, 204.21, 204.23, 204.24, 128/204.26
See application file for complete search history.

(56) References Cited

U.S. PATENT DOCUMENTS

| | | | |
|---|---|---|---|
| 5,134,995 A | 8/1992 | Gruenke et al. | |
| 5,245,995 A | 9/1993 | Sullivan et al. | |
| 5,303,699 A | 4/1994 | Bonassa et al. | |
| 5,353,788 A | 10/1994 | Miles et al. | |
| 5,492,113 A | 2/1996 | Estes et al. | |
| 5,503,146 A | 4/1996 | Froehlich et al. | |
| 5,551,419 A | 9/1996 | Froehlich et al. | |
| 5,598,838 A | 2/1997 | Servidio | |
| 5,632,269 A * | 5/1997 | Zdrojkowski | 128/204.23 |
| 5,694,923 A | 12/1997 | Hete et al. | |
| 5,735,267 A | 4/1998 | Tobia | |
| 5,813,399 A | 9/1998 | Isaza et al. | |
| 5,860,418 A | 1/1999 | Lundberg | |
| 6,213,119 B1 * | 4/2001 | Brydon | A61M 16/00 128/204.18 |
| 6,305,372 B1 | 10/2001 | Servidio | |
| 6,332,463 B1 | 12/2001 | Farrugia et al. | |
| 6,367,474 B1 | 4/2002 | Berthon-Jones | |
| 6,425,395 B1 | 7/2002 | Brewer et al. | |
| 6,536,432 B2 | 3/2003 | Truschel | |
| 6,571,599 B1 * | 6/2003 | Surjadi | A61M 16/00 73/1.62 |
| 6,571,795 B2 * | 6/2003 | Bourdon | 128/204.23 |
| 6,581,601 B2 * | 6/2003 | Ziaee | A61M 16/06 128/206.21 |
| 6,629,531 B2 * | 10/2003 | Gleason | A62B 18/08 128/205.25 |
| 6,817,361 B2 | 11/2004 | Berthon-Jones | |
| 7,013,361 B2 | 3/2006 | Liron | |
| 7,044,129 B1 * | 5/2006 | Truschel et al. | 128/204.23 |
| 7,137,389 B2 | 11/2006 | Berthon-Jones | |
| 7,270,128 B2 | 9/2007 | Berthon-Jones | |
| 7,438,073 B2 * | 10/2008 | Delache et al. | 128/204.23 |
| 7,469,698 B1 | 12/2008 | Childers | |
| 7,483,073 B2 | 1/2009 | Takai | |
| 7,487,774 B2 | 2/2009 | Acker | |
| 7,717,113 B2 | 5/2010 | Andrieux | |
| 7,770,579 B2 | 8/2010 | O'Connor et al. | |
| 7,987,847 B2 | 8/2011 | Wickham et al. | |
| 8,069,854 B2 | 12/2011 | Colla et al. | |
| 2004/0003814 A1 * | 1/2004 | Banner | A61M 16/04 128/204.21 |
| 2008/0196723 A1 | 8/2008 | Tilley | |
| 2008/0283060 A1 * | 11/2008 | Bassin | A61M 16/0051 128/204.18 |
| 2009/0241955 A1 | 10/2009 | Jafari et al. | |
| 2009/0301488 A1 | 12/2009 | Sun | |
| 2010/0078024 A1 | 4/2010 | Andrieux et al. | |
| 2010/0170513 A1 | 7/2010 | Bowditch et al. | |
| 2010/0180895 A1 | 7/2010 | Kwok et al. | |
| 2010/0319691 A1 | 12/2010 | Lune et al. | |
| 2011/0126832 A1 * | 6/2011 | Winter et al. | 128/204.21 |
| 2011/0126834 A1 | 6/2011 | Winter et al. | |
| 2011/0126835 A1 | 6/2011 | Winter et al. | |
| 2011/0209706 A1 | 9/2011 | Truschel et al. | |
| 2011/0277765 A1 | 11/2011 | Christopher et al. | |

OTHER PUBLICATIONS

European Search Report for EP 13 75 4710 dated Aug. 4, 2015.
Extended European Search Report for EP13755704.7, dated Dec. 3, 2015.
Examination Report for EP 13 755 704.7 dated Jun. 21, 2017.
Chinese Office Action for CN201480027861.7; dated Jul. 30, 2018.

* cited by examiner

DUAL PRESSURE SENSOR CONTINUOUS POSITIVE AIRWAY PRESSURE (CPAP) THERAPY

CROSS-REFERENCE TO RELATED APPLICATIONS

Not Applicable

STATEMENT RE: FEDERALLY SPONSORED RESEARCH/DEVELOPMENT

Not Applicable

BACKGROUND OF THE INVENTION

Field of the Invention

The present disclosure relates generally to the treatment of respiratory and cardiovascular conditions, and more particularly, to methods and systems for continuous positive airway pressure (CPAP) therapy selectively providing a pressurized flow of breathable gas to a patient utilizing dual pressure sensors at a source and on a ventilation mask.

Description of the Related Art

Mechanical ventilators comprise medical devices that either perform or supplement breathing for patients. Early ventilators, such as the "iron lung," created negative pressure around the patient's chest to cause a flow of ambient air through the patient's nose and/or mouth into the lungs. However, the vast majority of contemporary ventilators instead use positive pressure to deliver gas to the patient's lungs via a patient circuit between the ventilator and the patient. The patient circuit typically consists of one or two large bore tubes (e.g., 22 mm inner diameter for adults; 15 mm inner diameter for pediatrics) that interface to the ventilator on one end and a patient mask on the other end.

Ventilators may support either a single limb or a dual limb patient circuit. Single limb patient circuits are typically utilized for less acute clinical requirements such as the treatment of obstructive sleep apnea or respiratory insufficiency. In further detail, the single limb patient circuit, as its nomenclature suggests, involves gas flow from the ventilator to the patient and patient mask over a single conduit. The patient inspires fresh gas from the patient circuit, and expires carbon dioxide-enriched gas that is purged from the system through vent holes in the mask.

One particular application of ventilator devices is in the treatment of obstructive sleep apnea (OSA) syndrome, where the patient's upper airway narrows or collapses during sleep. There are repetitive pauses in breathing that may extend in duration up to half a minute. Although some degree of apnea is considered normal, in more severe cases, daytime sleepiness and fatigue may result as a consequence of reduced blood oxygen saturation, as well as constant interruptions to sleep cycles. In order to retain the patient's airway and ensure normal, uninterrupted breathing during sleep, continuous positive airway pressure (CPAP) therapy may be prescribed.

Generally, CPAP involves the application of positive pressure to open the patient's airway to prevent its collapse, as would otherwise occur during apnea. In a basic implementation, CPAP therapy applies a constant pressure that is not tied to the patient's normal breathing cycle. The positive airway pressure is desired in the inspiratory phase when the pressure differences between the lungs and the nose contribute to the collapse of the intermediate airway. However, supplying positive pressure flow into the patient during the expiratory phase generates resistance to the patient's breathing efforts, causing discomfort. Furthermore, toward the end of the patient's expiratory phase, flow and pressure in the airway is naturally minimal, such that positive pressure can cause additional discomfort. Notwithstanding the clinician's best efforts to prescribe a CPAP treatment flow rate that minimizes such extraneous pressure augmentation while ensuring the proper splinting of the airway during inspiration, the patient is still subject to higher pressures than needed throughout the breathing cycle.

Partially in response to this deficiency, CPAP systems that varied the pressure augmentation depending on the patient flow, i.e., inspiration or expiration, were developed. One such system is described in U.S. Pat. No. 6,932,084 to Estes, et al., which is understood to involve pressure augmentation during inspiration and pressure relief during exhalation based upon a patient flow estimator. The delivered pressure, which itself is measured and utilized by a pressure controller in a feedback loop to confirm accuracy, is calculated as a function of a constant CPAP prescription pressure and a proportional value of patient flow. A relief or augmentation constant defines the degree thereof, and the patient flow is estimated. The value of the constant is zero during inspiration, thus providing no pressure augmentation and the delivered pressure is equivalent to the base or prescription pressure. During expiration, the value of the constant is non-zero, and the pressure delivered to the patient is the prescription pressure less a proportional amount of the estimated instantaneous patient flow. A signal representative of the delivered pressure drives the blower hardware delivering therapeutic air flow to the patient. Although the method disclosed by Estes, et al. allows the delivered therapeutic pressure to the patient to be tuned to a greater degree, the patient nevertheless experiences discomfort.

Another approach to the issue of excess pressure at the expiration stage is disclosed in U.S. Pat. No. 7,128,069 to Farrugia et al. When a transition from the inspiration phase to the expiration phase is detected, i.e., when the pressure at the patient's mouth begins to drop, the motor that controls the blower is understood to be de-energized and allowed to free-wheel. After the pressure increases back to a predetermined level, which in the Farrugia et al. disclosure is 3 cm $H_2O$, the blower motor is restarted to bring the pressure at the patient's mouth to prescription levels (10 cm $H_2O$). Thus, the temporary stopping of the blower is understood to function as a pressure relief during expiration. However, due to the wind-up and wind-down times associated with starting and stopping an electrical motor, patient comfort is not optimized due to the existence of residual pressure.

Accordingly, there is a need in the art for improved methods and systems for continuous positive airway pressure (CPAP) therapy including the use dual pressure sensors at a source and on a ventilation mask to control an exhalation valve.

BRIEF SUMMARY OF THE INVENTION

In accordance with one embodiment of the present disclosure, there is contemplated a respiratory assistance device. There may be a blower with an output, in addition to a patient ventilation interface that can be configured for fitment on a patient respiratory passageway. The patient ventilation interface may also include a piloted exhalation valve. Furthermore, there may be a gas passage conduit that couples the output of the blower to the patient ventilation interface. A pilot line from the gas passage conduit may be coupled to the pilot of the exhalation valve. The respiratory assistance device may also include a first pressure sensor that can measure a blower pressure at the output of the blower, as well as a second pressure sensor that can measure a mask pressure in the patient ventilation interface. There may be a pressure controller that is in communication with the first pressure sensor and the second pressure sensor that can detect a patient inspiratory phase and a patient expiratory phase based upon pressure differentials between the mask pressure and the blower pressure. The pressure controller can regulate therapeutic airflow delivered to the patient and exhausted through the piloted exhalation also based upon such pressure differentials. Furthermore, the pressure controller may relieve mask pressure by reducing therapeutic airflow delivered to the patient according to a function of the blower pressure.

In accordance with another embodiment of the present disclosure, there is a continuous positive airway pressure (CPAP) apparatus for respiratory assistance of a patient. The apparatus may include a blower having an output connectible to a ventilation mask that is wearable by the patient. There may also be a first pressure sensor that can measure blower pressure at the output of the blower as generated by the blower, in addition to a second pressure sensor that is connectible to the ventilation mask for measuring mask pressure therein. The apparatus may further include a pressure controller that can be connected to the first pressure sensor and the second pressure sensor. A patient inspiratory phase and a patient expiratory phase may be detectable by the pressure controller to regulate therapeutic pressure corresponding to the generated blower pressure at the patient based upon pressure differentials between the mask pressure and the blower pressure.

According to yet another embodiment of the present disclosure, there is contemplated a method for administering continuous positive airway pressure (CPAP) therapy to a patient. The method may begin with receiving a first CPAP therapeutic pressure value. There may also be a step of measuring a blower pressure value at an output of a blower that generates blower pressure for the patient. Additionally, there may be a step of measuring a mask pressure value at a ventilation mask that is worn by the patient. The method may further include generating a pressure differential value from the blower pressure value and the mask pressure value, and then evaluating a patient respiratory state from the pressure differential value. The patient respiratory state may be one of an inspiration state and an expiration state. The method may further include selectively applying a quantity of the blower pressure to the patient as therapeutic pressure in response to the evaluated patient respiratory state. The quantity of the blower pressure generated by the blower may correspond to the first CPAP therapeutic pressure value.

The present disclosure will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which like numbers refer to like parts throughout, and in which:

FIG. 8 is a pressure diagram graphically illustrating the pressure at the blower device and a pressure relief target; and.

Common reference numerals are used throughout the drawings and the detailed description to indicate the same elements.

DETAILED DESCRIPTION OF THE INVENTION

The detailed description set forth below in connection with the appended drawings is intended as a description of the several presently contemplated embodiments of a system for continuous positive airway pressure (CPAP) therapy. The system delivers breathing gas to a patient for the treatment of obstructive sleep apnea (OSA) and other cardio-pulmonary conditions, and implements various methods for the selective pressure augmentation and relief throughout the breathing cycle. This description is not intended to represent the only form in which the disclosed invention may be developed or utilized. The description sets forth the functions and features in connection with the illustrated embodiments. It is to be understood, however, that the same or equivalent functions may be accomplished by different embodiments that are also intended to be encompassed within the scope of the present disclosure. It is further understood that the use of relational terms such as first and second and the like are used solely to distinguish one from another entity without necessarily requiring or implying any actual such relationship or order between such entities.

Figure 1:
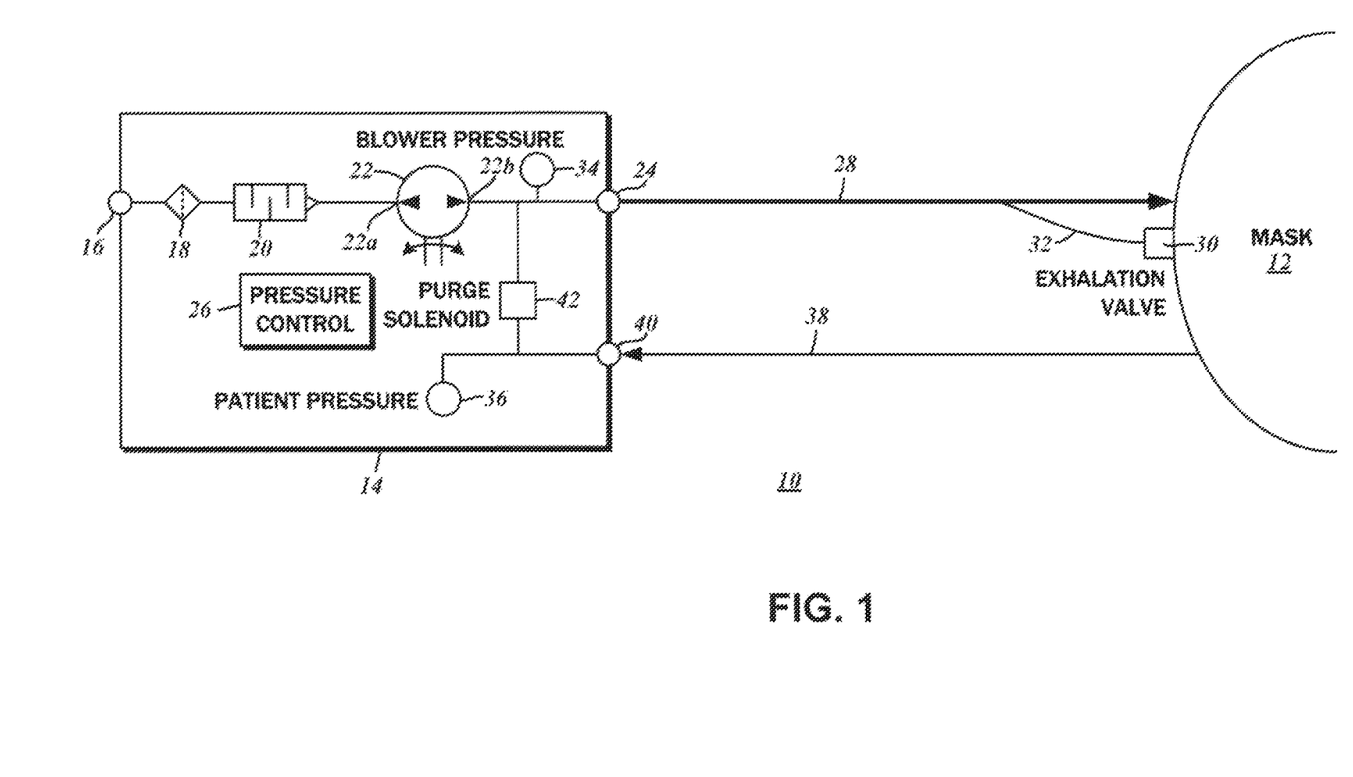
FIG. 1 is a block diagram showing the various components of a CPAP apparatus in accordance with various embodiments of the present disclosure including a ventilation unit, a patient ventilation mask, and gas passage conduits.

With reference to the block diagram of FIG. 1, one embodiment of the present disclosure contemplates a CPAP system 10 generally comprised of a patient ventilation interface 12 and a ventilation unit 14. The patient ventilation interface 12 may include such devices as a full-face mask or a nasal mask that can be placed in direct gas flow communication with the upper respiratory tract of the patient, i.e., the nasal cavity and the oral cavity. One embodiment of the CPAP system 10 may utilize a nasal mask such as that described in co-pending U.S. patent application Ser. No. 13/411,348 entitled VENTILATION MASK WITH INTEGRATED PILOTED EXHALATION VALVE filed Mar. 2, 2012, now issued U.S. Pat. No. 8,844,533, and U.S. patent application Ser. No. 13/411,407 entitled VENTILATION MASK WITH INTEGRATED PILOTED EXHALATION VALVE, filed Mar. 2, 2012, now issued U.S. Pat. No. 8,839,791, the disclosures of which are hereby incorporated by reference in their entireties herein. It will be appreciated that other apparatuses that so interface the respiratory system of the patient to the ventilation unit 14 may be substituted without departing from the scope of the present disclosure, so long as certain features noted below are incorporated.

Generally, the ventilation unit 14 generates a flow of breathing gas that is delivered to the patient via the patient ventilation interface 12. The breathing gas may be ambient air, a combination of ambient air enriched with oxygen, or any other suitable mixture of gas appropriate for treating the patient. Those having ordinary skill in the art will recognize the variety of options for mixing breathing gasses before delivery to the patient. In further detail, the ventilation unit 14 includes a first inlet port 16, through which ambient air is drawn. The first inlet port 16 is in communication with an inlet filter 18 that removes particulates and other contaminants from the breathing gas that is ultimately delivered to the patient. Optionally, in line with the inlet filter 18 is a sound suppressor 20 that reduces the sound of gas flow through the ventilation unit 14.

The force needed for drawing the ambient air through the first inlet port 16, the inlet filter 18, and the sound suppressor 20 is provided by a centrifugal fan or blower 22. In this regard, the blower has a blower inlet port 22a coupled to the sound suppressor 20, and a blower outlet port 22b that is in gas flow communication with an outlet port 24 of the ventilation unit 14. It will be recognized that any suitable blower 22 capable of generating the gas flow and pressure suitable for CPAP treatment in accordance with the present disclosure may be utilized. The blower 22 is driven electrically and its actuation is governed by a programmable pressure controller 26, which implements the various methods of CPAP treatment contemplated by the present disclosure as will be described in further detail below.

The flow of breathing gas that is output from the blower 22 is passed through the outlet port 24 to a gas conduit 28 that is in coupled to the aforementioned mask or patient ventilation interface 12. The gas conduit 28 is understood to be a plastic tube having a predetermined inner diameter such as 22 mm or smaller, though any other conduit of suitable material and construction may be utilized. The patient ventilation interface 12 in accordance with various embodiments of the present disclosure also includes a piloted exhalation valve 30 that is selectively actuated depending on the pressure differential between the patient ventilation interface 12 and the ventilation unit 14. The exhalation valve 30 is connected to a pilot line 32 that branches from the gas conduit 28. A pressure difference is generated between the patient ventilation interface and the exhalation valve, such that it is closed during inspiration and opened during expiration.

In order to ascertain such pressure differentials, the presently contemplated CPAP system 10 includes dual pressure sensors, including a device pressure sensor 34 and a mask pressure sensor 36. The device pressure sensor 34 is disposed within the ventilation unit 14, and monitors the pressure at the blower outlet port 22b. The mask pressure sensor 36 is also physically disposed within the ventilation unit 14, but is in direct gas flow communication with the mask or patient ventilation interface 12 over a pressure sensor line 38 that is connected to a second inlet port 40. When the ventilation unit 14 is operating, gas pressure within the pressure sensor line 38 as well as the gas conduit 28 may be connected to deliver a purge flow to clear line 38. This can be done through a purge solenoid 42 connected to both. The purge can be continuous or intermittent according to the patient's breathing phase or pressure difference between the blower pressure and the mask pressure.

Figure 2:
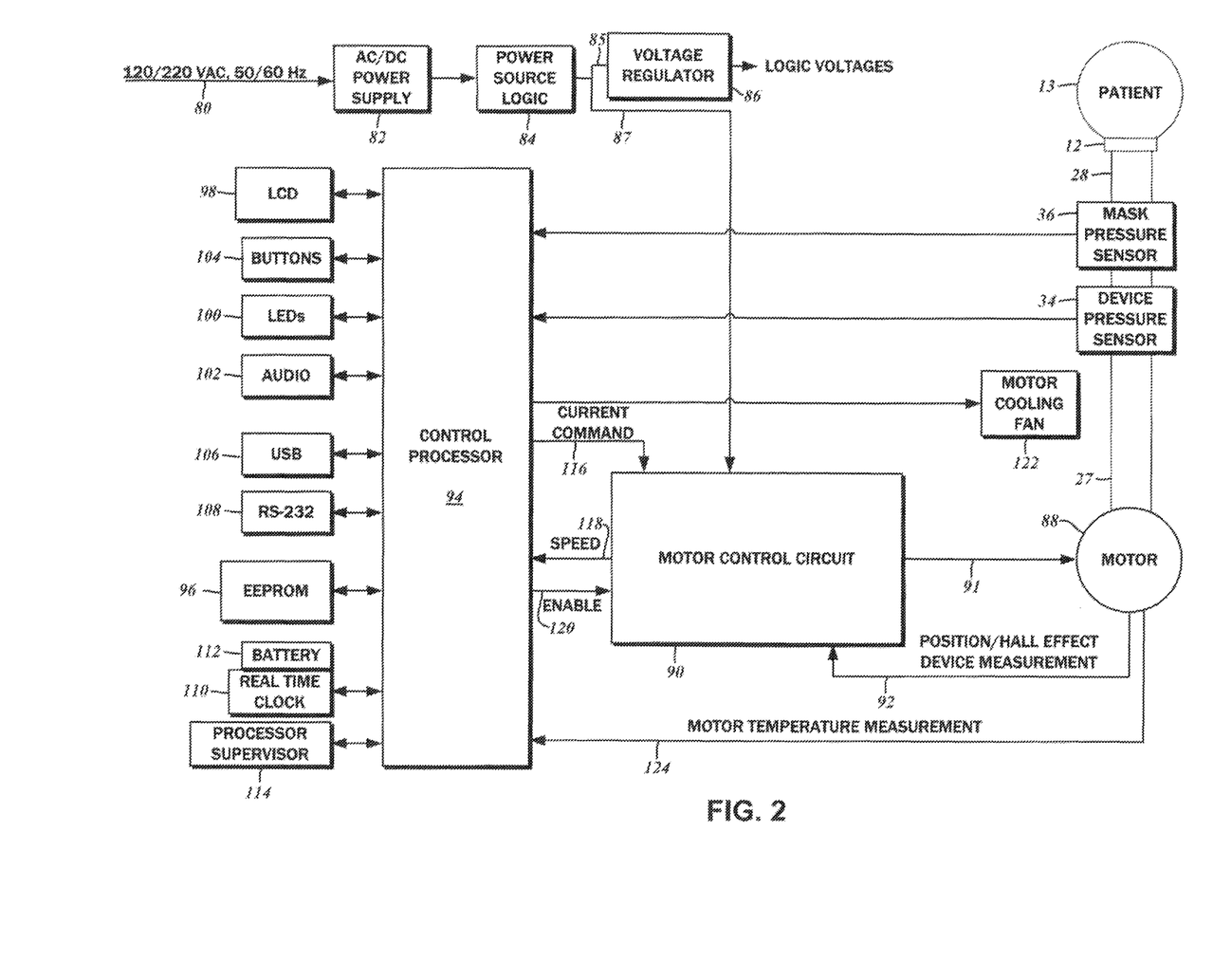
FIG. 2 is a block diagram illustrating the electrical components of the ventilation unit.

The block diagram of FIG. 2 illustrates the various electrical components of the ventilation unit 14. Power for the ventilation unit 14 may be provided from a conventional household electricity supply of either 120V or 220V alternating current (AC), at 50 Hz or 60 Hz. The block diagram denotes this supply as a power source 80. A power supply 82 is connected to the power source 80, and as will be recognized by those having ordinary skill in the art, the power signal is variously rectified, filtered, and stepped down to a direct current (DC) voltage. In accordance with one embodiment of the present disclosure, the DC voltage source is 24 V. It is understood that the blower 22 utilizes a higher DC voltage than control logic devices, and thus the power supply 82 is connected to a power source logic 84. A first output 85 of the power source logic 84 is connected to an integrated circuit voltage regulator 86 that steps down the DC voltage to the logic device level of 5V. A second output 87 of the power source logic 84 is the existing high DC voltage directly from the power supply 82, and is connected to the motor control circuit 90.

The blower 22 is comprised of several electrical components, including a motor 88 and a motor control circuit 90. In accordance with one embodiment, the motor 88 is a brushless DC or electrically commutated motor. It will be recognized that the speed of rotation of the motor 88 is based upon input logic signals provided to the motor control circuit 90, which drives electrical current through its windings that induce magnetic fields that translate to rotational motion of the attached rotor. A fan coupled to the rotor thus rotates and generates a flow of air through an internal conduit 27. The internal conduit 27 is coupled to an outlet port 27, which is coupled to the gas conduit 28. As described above, the device pressure sensor 34 and the mask pressure sensor 36 are connected to the pneumatic circuit between the motor 88 and a patient 13.

The motor control circuit 90 has a motor drive output 91 that is connected to the motor 88. The position of the motor 88 is detected by a Hall-effect sensor that is incorporated into the motor 88. An output voltage 92 from the Hall-effect sensor is fed back to the motor control circuit 90, which ensures that the actual position corresponds to the intended or commanded position.

The pressure controller 26 and its functionality may be implemented with a programmable integrated circuit device such as a microcontroller or control processor 94. Broadly, the control processor 94 receives certain inputs, and based upon those inputs, generates certain outputs. The specific methods that are performed on the inputs may be programmed as instructions that are executed by the control processor 94. In this regard, the control processor 94 may include an arithmetic/logic unit (ALU), various registers, and input/output ports. Although external memory such as EEPROM (electrically erasable/programmable read only memory) 96 may be connected to the control processor 94 for permanent storage and retrieval of program instructions, there may also be an internal random access memory (RAM). One embodiment contemplates the use of an Intel 8081 instruction set/architecture, though any other suitable instruction set or processor architecture may be substituted. As indicated above, the control processor 94 is powered by a low voltage DC supply from the voltage regulator 86.

Several output devices are envisioned for the ventilation unit 14. In order to set the operational parameters of the ventilation unit, and to initiate or terminate certain functions, a graphical user interface is provided. Such graphical user interface is generated on a display screen 98, which may be of a liquid crystal display (LCD) type. Any type of graphic may be shown on the display screen 98, though for more specific indicators, a simple light emitting diode (LED) device 100 may be utilized. It will be recognized that alarm conditions, power status, and the like may be indicated with the LED device 100. Along these lines, audible outputs may be produced with audio transducers 102 that are likewise connected to the control processor 94. Among the contemplated outputs that may be generated on the audio transducer 102 include simple beeps and alarms, as well as sophisticated voice prompts that provide information and instructions.

An operator may interact with the graphical user interface through different input devices such as buttons 104 that are connected to the input ports of the control processor 94. It is understood that the audio transducer 102 may also accept sound input in the form of voice commands, the processing of which is performed may be performed by the control processor 94. Similarly, the display screen 98 may be incorporated with touch sensors, and may also function as an input device that allows an operator to interact with the graphical user interface displayed thereon.

Several modalities for connecting to and communicating with other data processing devices such as general-purpose computers are also contemplated. Accordingly, the control processor 94 may be connected to a universal serial bus (USB) controller 106. For more basic communications, there may be a serial RS-232 transceiver 108. Through these data communications modalities, the configuration options of the ventilation unit 14 may be set, operating profiles may be downloaded, and so forth.

The functions of the ventilation unit 14 depend on proper synchronization, and so the control processor 94 is connected to a real time clock 110 that maintains a common clock cycle. Although a primary feature of the real time clock 110 is to maintain synchrony at a processor cycle level, longer term time data is also maintained. In order to retain such time data, the real time clock 110 may be powered independently of the primary power source 80, and there is accordingly a battery backup 112. Under heavy processing loads or unexpected program conditions, the control processor 94 may become unable to execute critical programmed steps in real-time. Thus, the control processor 94 may include a processor supervisor 114 that invokes a program execution break upon detecting such conditions. Typically, this is implemented as a step of clearing a memory variable periodically, and when that step is unable to take place because instruction execution is frozen or otherwise delayed, the processor supervisor 114 may cause a predetermined routine to be executed.

As indicated above, the motor 88 is driven by the motor control circuit 90, which generates different outputs depending on signals received from the control processor 94. The signal to drive the motor 88 is generated on a current command line 116. For control processing on a broader level, feedback from the blower 22 is utilized, and in the specific form of a speed measurement input 118 from the motor control circuit 90. Furthermore, as detailed below, pressure readings at the blower 22 and the patient 13 are utilized to reach control decisions. Accordingly, the device pressure sensor 34 and the mask pressure sensor 36 are both connected to the control processor 94. The blower 22 is activated and deactivated via a motor enable line 120. To ensure that the temperature of the motor 88 remains within operational parameters, a motor cooling fan 122 is driven directly by the control processor 94. In some embodiments, there may be additional control circuitry that isolates the power source of the motor cooling fan 122 from the control processor 94. The decision to activate and deactivate the motor cooling fan 122 is made in response to temperature readings from the motor 88, and there is a motor temperature reading 122 passed to the control processor 94.

Figure 3:
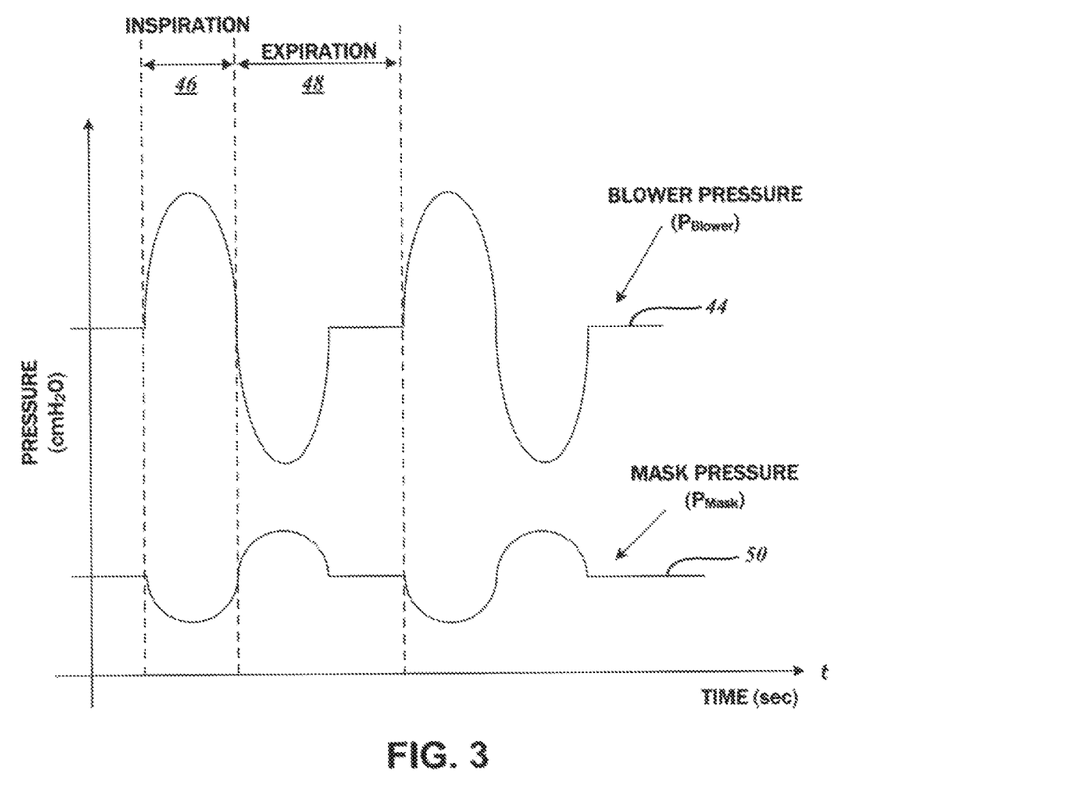
FIG. 3 is a pressure diagram graphically illustrating the pressure cycles at the blower and the patient mask over a typical breathing sequence including inspiratory phases and expiratory phases.

Referring now to the pressure diagram of FIG. 3, the typical operating pressures at the blower 22 and at the patient mask at different points in the breathing cycle is illustrated. More particularly, a first plot 44 illustrates the pressure cycle at the blower 22, and is characterized by an inspiration region 46 and an expiration region 48. As will be appreciated, the pressure at the blower 22 increases during inspiration, and decreases during expiration. Henceforth, the first plot 44 and the measurement represented thereby will be referred to as $P_{Blower}$, with the pressure value at any particular time t being referred to as $P_{Blower}(t)$. This pressure is given in terms of $cmH_2O$, as are the other pressure measurements discussed herein.

The mask pressure at the patient will exhibit an opposite response, where it decreases in the inspiration region 46 and increases in the expiration region 48. A second plot 50 illustrates the pressure cycle at the patient ventilation interface 12, and is similarly characterized by the inspiration region 46 and the expiration region 48. The second plot 50 and the measurement represented thereby will be referred to as $P_{Mask}$, with the pressure value at any particular time t being referred to as $P_{Mask}(t)$. As can be seen, the pressure at the blower 22 $P_{Blower}$ is significantly higher than the pressure at the patient ventilation interface 12 $P_{Mask}$, and the two values are generally reciprocal. That is, when $P_{Mask}$ peaks, $P_{Blower}$ is at its lowest, and vice versa. As referenced herein, the terms patient ventilation interface 12 and patient mask are utilized interchangeably. It will be recognized that the patient mask is a specific kind of patient ventilation interface, and as explained briefly above, other types of ventilation interfaces may be utilized. Along these lines, reference to such terms as mask pressure, blower pressure, or the use of the term mask or blower to modify any other term is for purposes of convenience only and not of limitation. For instance, mask pressure is understood to refer to the pressure in the patient ventilation interface 12, while blower pressure refers to the pressure at the output of the blower 22.

Figure 4:
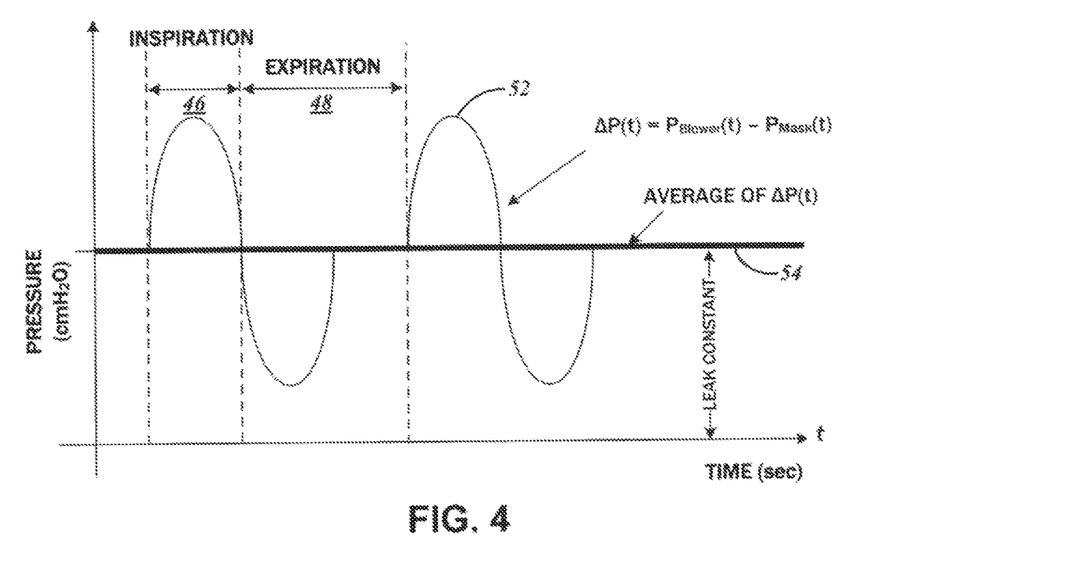
FIG. 4 is a pressure diagram graphically illustrating the pressure cycle differences (ΔP) at the blower and the patient mask over the breathing sequence.

In accordance with various embodiments of the present disclosure, patient leak indication is contemplated. As shown in the graph of FIG. 4, a first plot 52 is representative of the difference between $P_{Blower}$ and $P_{Mask}$ over a time period at a given instant, and is also referred to as ΔP. The first plot 52 can also be characterized by the inspiration region 46 and an expiration region 48. The average of the pressure difference ΔP is represented as a leak constant 54. It will be recognized that the larger the value of the leak constant 54, the greater the leakage.

Figure 5:
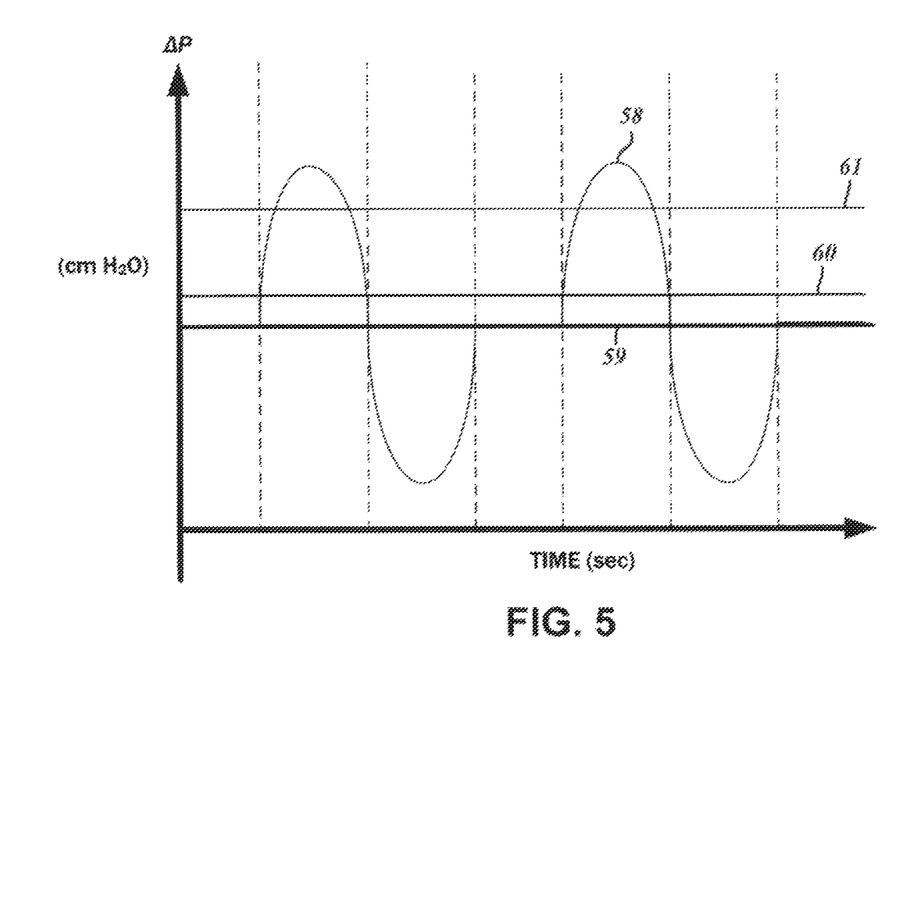
FIG. 5 is a pressure diagram graphically illustrating the pressure difference (ΔP) at the blower device and the patient mask with a superimposed threshold that defines when an exhalation valve is opened or closed.

Referring now the graph of FIG. 5, the determination of the patient trigger and cycle states will now be considered. It is understood that cycling and trigger states are based on the patient's breathing cycle, and so the present disclosure contemplates a modality by which the inspiration phase and the expiration phase can be ascertained. A plot 58 represents the pressure difference ΔP between the mask pressure $P_{Mask}$ and the blower pressure $P_{Blower}$ over a time period.

In accordance with one embodiment, a trigger limit 60 is set or otherwise computed as an average 59 of ΔP. More particularly, the trigger limit 60 at time (t) may be the average ΔP also at time (t) plus a predetermined trigger constant, which may be set by the clinician or the patient. If the pressure difference ΔP at (t) is greater than the trigger limit at the same time (t), the patient is considered to be in the inspiration phase.

A cycle limit 61 is also set, and is understood to be a function of the peak value of ΔP. In further detail, the cycle limit at time (t) is the maximum ΔP at time (t) multiplied by a cycle constant. The cycle constant can also be set by the clinician or the patient, or otherwise computed as a function of ΔP(t). If the measured ΔP is less than the set cycle limit, then the patient is determined to be in the expiration phase.

Figure 6:
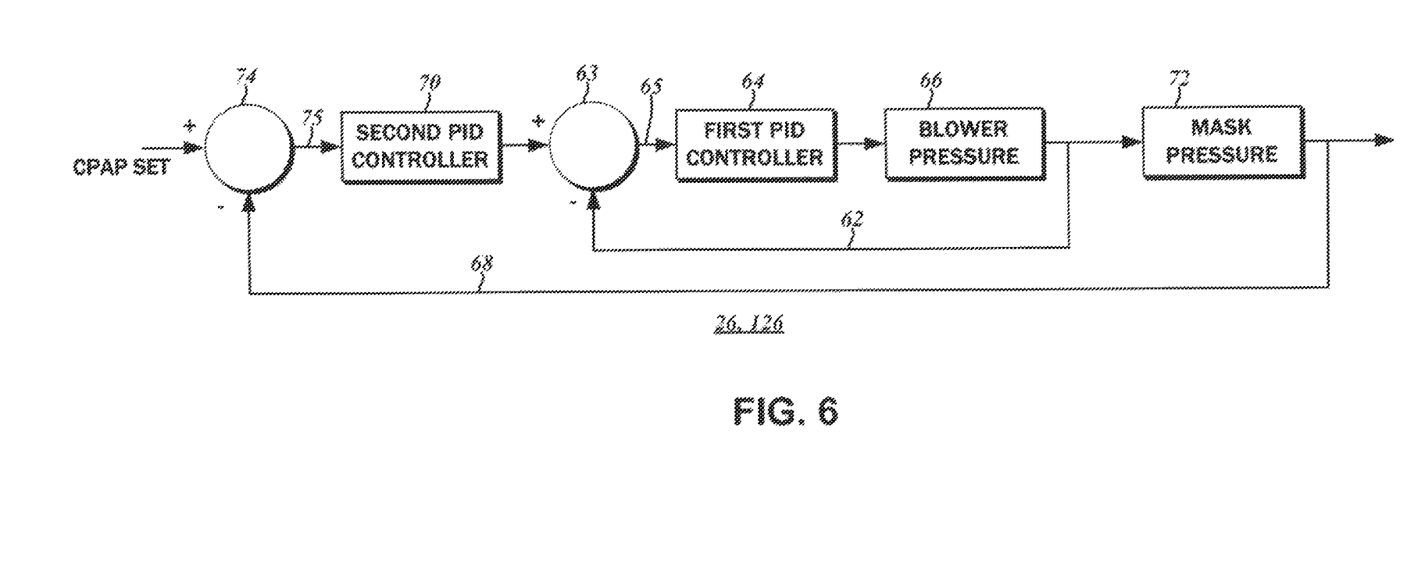
FIG. 6 is a control loop block diagram depicting pressure sensor variables corresponding to the blower and a mask as inputs to control devices.

The specific pressure that is to be delivered to the patient by way of the blower 22 is set by the programmable pressure controller 26, and FIG. 6 is a control loop block diagram thereof. The piloted exhalation valve 30 further provides pressure relief depending on the current pressure difference between the blower pressure and the mask pressure ($\Delta P(t) = P_{Blower}(t) - P_{Mask}(t)$), the details pertaining to the operation of which will be discussed more fully below. The exhalation valve 30 is configured to open to ambient pressure when the pressure difference (ΔP) is small or negative, and closes when pressure difference (ΔP) is sufficiently high.

Still referring to the control loop block diagram of FIG. 6, additional details pertaining to the motor control functions of the blower 22, and specifically the closed loop control circuit 126, will now be considered. Generally, the closed loop control circuit 126 includes the first PID controller 64, and a second PID controller 70, both of which act upon the motor 88 to effectuate pressure changes within the patient circuit. There is a first or inner control loop 62 that is driven by the first PID controller 64 to modulate blower pressure 66, as well as a second or outer control loop 68. Together with the first PID controller 64 and the second PID controller 70, mask pressure 72 is modulated. The inner control loop 62 and the outer control loop 68 are inter-related and together define the closed loop control circuit 126.

One objective of the closed loop control circuit 126 is to operate the blower 22 to the extent necessary to achieve a predetermined pressure sufficient to meet the inspiratory pressure demands of the patient and the pressure losses in the ventilation system 14. A desired pressure, which is the preset CPAP pressure as input by the clinician, is represented by an input value 73 that is provided to a first summing point 74. The pressure at the patient mask, i.e., mask pressure 72, is measured by pressure sensor as discussed above, and also input to the first summing point 74. An output signal 75 corresponding to the summed pressures of the input value 73 and the mask pressure 72 is passed to the second PID controller 70. The output signal 75 is processed by the second PID controller 70, and this processed signal is output to the motor control circuit 90 to partially regulate the blower 22 in response.

The output from the second PID controller 70 is input to a second summing point 63, which also adds the pressure value at the blower, i.e., the blower pressure 66. Another output signal 65 corresponding to these summed pressures is passed to the first PID controller 64, which again is processed and output to the motor control circuit 90 to regulate the blower 22. The subsequent blower pressure 66 measurement is again fed back to the second summing point 63, at which point the inner loop continues.

The first PID controller 64 is thus part of a closed loop control over a blower pressure 66, with the output thereof being the current set point for the blower 22. Furthermore, the second PID controller 70 minimizes the error between the mask pressure and the CPAP set level 73. The output of the second PID controller 70 is the set pressure for the first PID controller 64. The respective gains of the first PID controller 64 and the second PID controller 70 may be scheduled according to the patient breathing phase and/or the CPAP set level 73. During expiration, the pressure controller 26 can be reconfigured to control the speed of the blower 22, blower pressure, blower flow, either alone or to different set targets. Upon detecting an inspiration phase, the CPAP set level 73 can be set to a different value than during expiration, a technique known as Bi-level CPAP.

Figure 7:
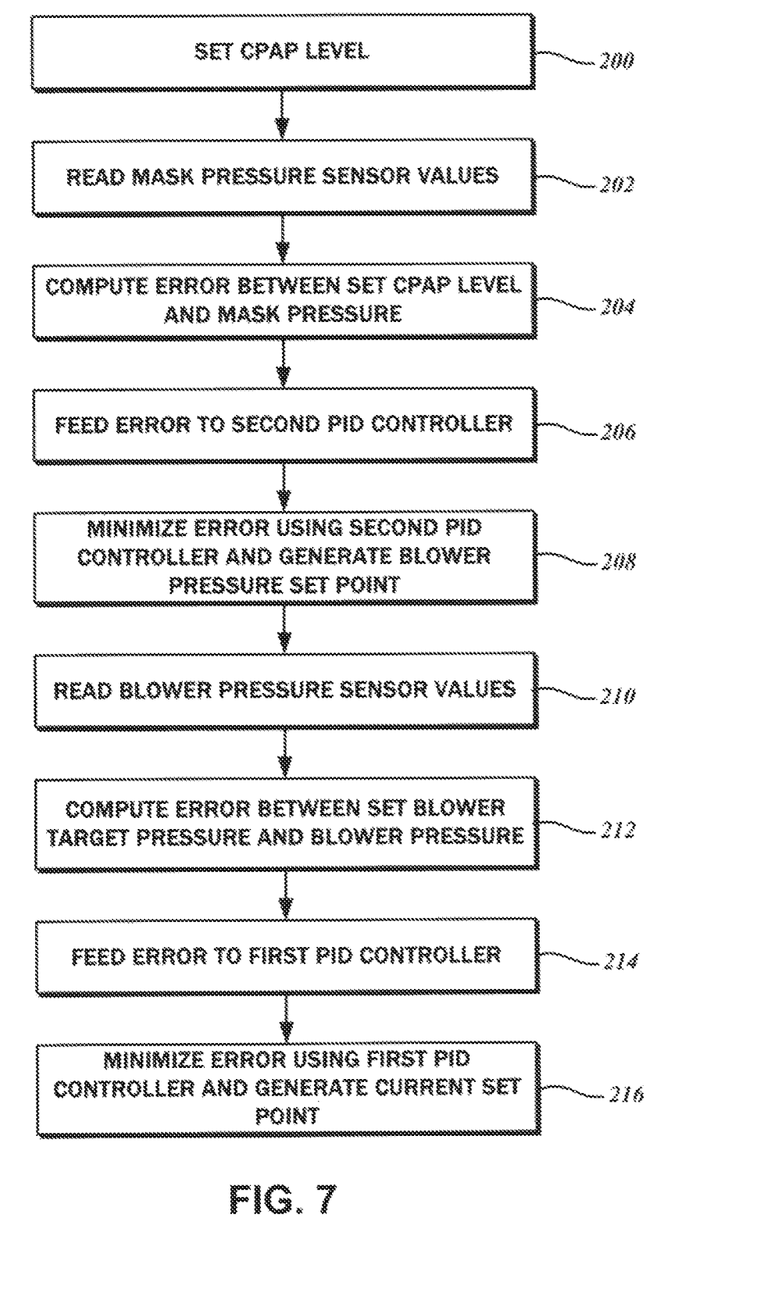
FIG. 7 is a flowchart illustrating the processing steps of the control loop shown in FIG. 6.

With reference to the flowchart of FIG. 7, the steps involved in the control loop circuit 126 will be described. In a step 200, the CPAP level 73 is set. The mask pressure 72 is then read in a step 202, and the error between the set CPAP level 73 and the mask pressure 72 is computed in a step 204, as described above in relation to the second summing point 74. In a step 206, the computed error is fed to the second PID controller 70. The blower 22 is modulated by the second PID controller 70 in a step 208 to minimize the error between the set CPAP level 73 and the mask pressure 72. At this point, the blower pressure set point is generated. Per the inner control loop 62, the blower pressure 66 is received in a step 210, and an error between such value and the set blower pressure set point from the second PID controller 70 is computed in a step 212. The amount of error is then fed to the first PID controller 64 in accordance with a step 214. The error is minimized by further modulating the blower 22 in a step 216, thereby generating the current set point.

The pressure relief target is understood to be a function of the blower pressure or ΔP. The pressure diagram of FIG. 8 includes a plot 78 of the pressure $P_{Blower}(t)$ over a breathing cycle. During the time the blower pressure is lower than average ΔP (t), the mask pressure target is also reduced to create a pressure relief 80. For improved patient comfort, pressure at the patient could be further reduced according to a function of the blower pressure. The target mask pressure at time (t) is contemplated to be the set CPAP level 73 during the inspiration phase. During the expiration phase, the target pressure at time (t) is contemplated to be the set CPAP level 73 reduced by the blower pressure $P_{Blower}(t)$ multiplied by a relief constant. The relief constant and a minimum mask pressure level may also be set.

Figure 8:
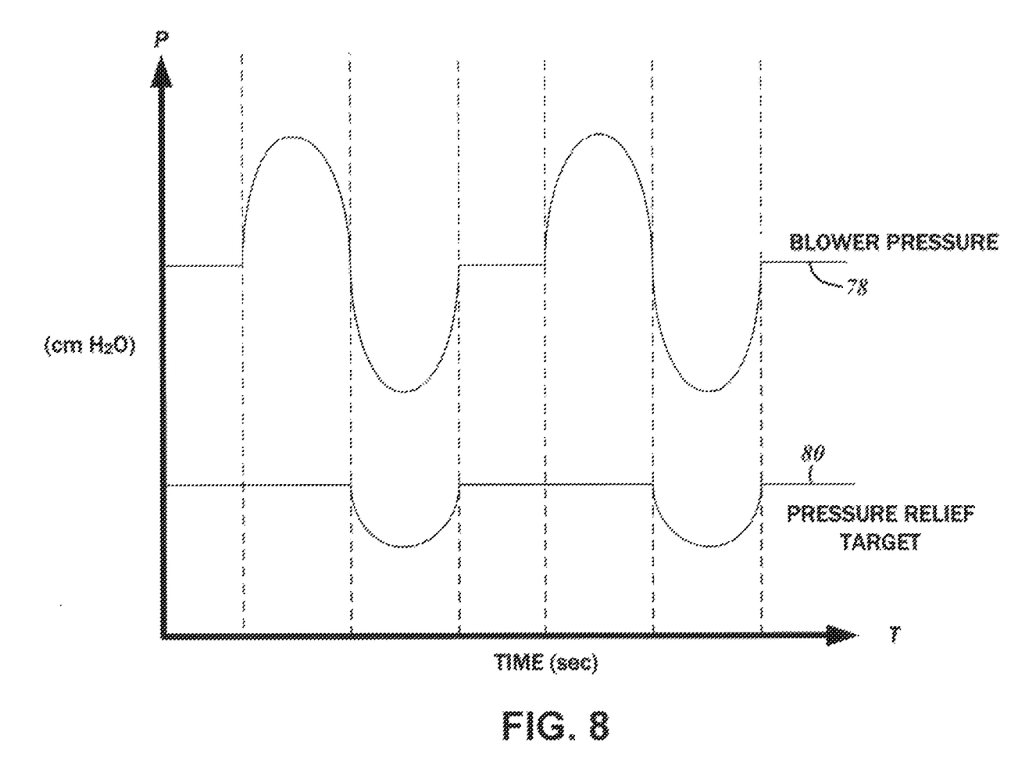

The blower 22 can be triggered upon the pressure difference ΔP(t) reaching the triggering threshold pressure level 60, that is, pressure augmentation during the inspiratory phase may be initiated by the patient's spontaneous breathing until the pressure difference reaches such threshold. In further detail, the blower 22 is triggered upon the pressure difference ΔP(t) increases from a level lower than the triggering threshold pressure level 60 to a level higher than the same (a positive d(t)). The triggering threshold pressure level 60 can be adjusted manually. Alternatively, an average threshold value may be calculated based upon previous breathing cycle patterns and set, and such breathing cycle patterns may be leak constant. In this regard, the triggering threshold pressure level 60 may be continuously adjusted to adapt to the patient's respiratory functions. Different embodiments further contemplate wave shape triggering, gas volume triggering, and a flow triggering, with the integral of flow being understood to be volume.

With regard to flow triggering, it will be appreciated by those having ordinary skill in the art that flow sensors are typically cost-prohibitive. In combination with the aforementioned dual pressure sensor ventilation method, the blower 22 can be triggered from estimated flow. It is understood that breathable gas flow to the patient may be estimated from the speed of the blower 22, and the detected pressure levels. The corresponding flow values may be stored in a lookup table or other like data structure. How much flow a particular blower 22 can generate depends on the configuration thereof, so multiple data sets for different blowers 22 may be developed and stored.

It is also contemplated that a cycling threshold pressure level 61 may be set. When the patient's breathing cycles between the inspiratory phase and the expiratory phase, delivery of the therapeutic gas flow is stopped. The point at which this occurs is the cycling threshold pressure level 61, and so when the pressure difference ΔP(t) transitions from a level higher than the cycling threshold pressure level 61 to a level lower than the same (a negative d(t)), the blower 22 is cycled. The cycling threshold pressure level 61 is understood to be set higher than the triggering threshold pressure level 60.

Figure 9:
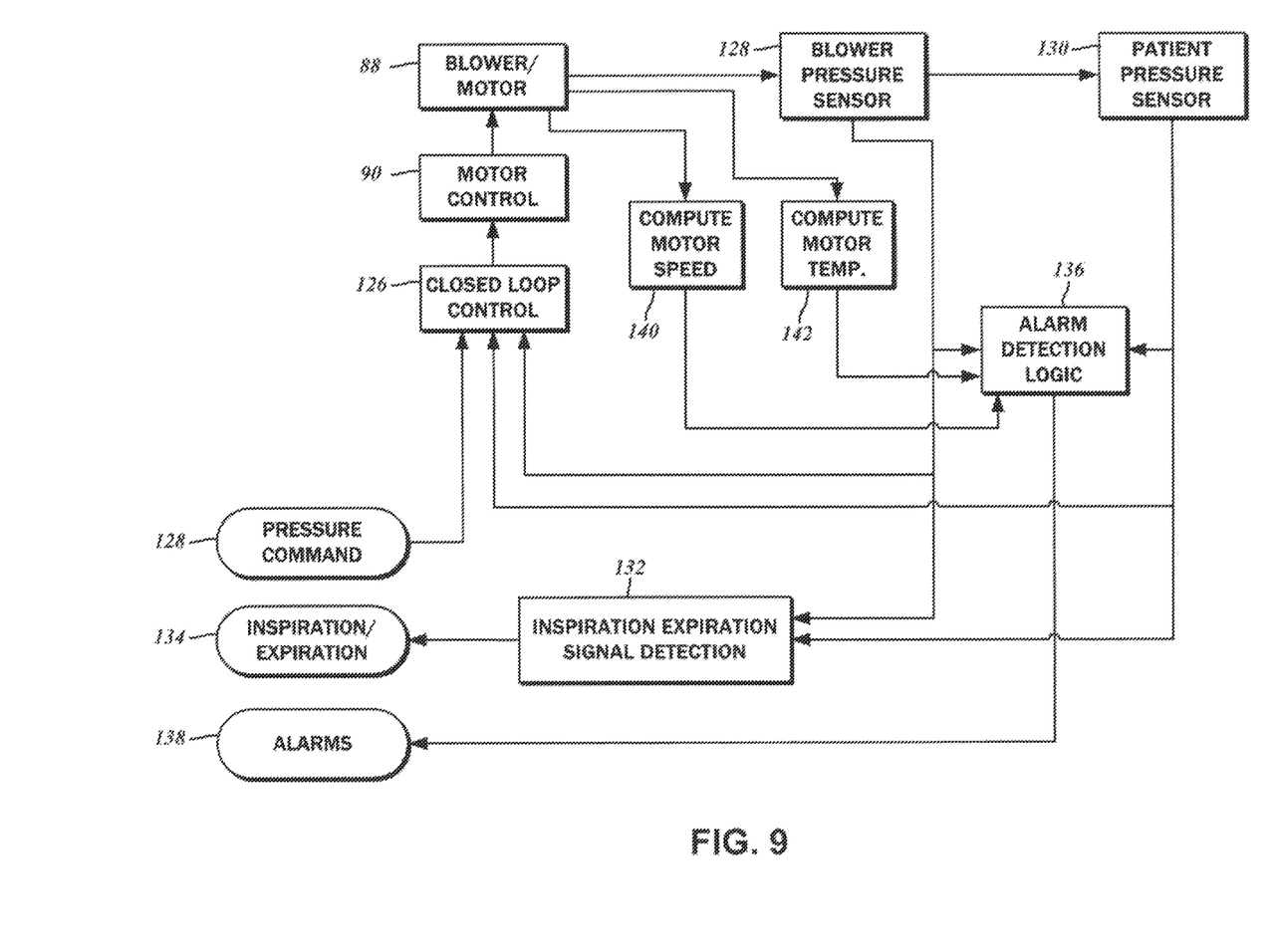
FIG. 9 is a block flow diagram showing the interrelated components of the ventilation unit.

With reference to the flow diagram of FIG. 9, the operational sequence of the CPAP system 10 will be considered. As indicated above, the motor 88 is driven by a motor control circuit 90, that is, electrical current is selectively applied by the motor control circuit 90 to the conductive elements of the motor 88 to induce a magnetic field that produces rotation. The specific sequence and manner in which the blower 22 (i.e., the motor 88 and the motor control circuit 90) is actuated is governed by a closed loop control circuit 126 that is implemented by the pressure controller 26. One of the inputs to the closed loop control circuit 126 is a pressure command 128, or the therapeutic pressure that is set by a clinician.

Actuating the motor 88 results in a change in pressure at the blower 22, as sensed in a device pressure sensor block 128. Furthermore, pressure readings are also made at the patient ventilation interface 12, or a mask pressure sensor block 130. These readings are inputs to the closed loop control circuit 126. Additionally, the readings from the device pressure sensor block 128 and the mask pressure sensor block 130 are utilized in a breathing cycle state detector block 132. As mentioned above, the pressure difference (ΔP) can be utilized to determine whether the patient 13 is in an expiration (exhalation) state or an inspiration (inhalation state). The breathing cycle state detector 132 so utilizes the pressure measurements and generates a breathing cycle state output 134.

Different alarm conditions may be evaluated based in part on the pressure difference between the measurements from the device pressure sensor block 128 and the mask pressure sensor block 130. These values are passed to an alarm detection logic block 136 that can trigger an alarm 138. Besides the pressure differences, the speed of the motor 88 is calculated in a motor speed evaluation block 140, and the temperature of the same is calculated in a motor temperature evaluation block 142. These calculated values are also passed to the alarm detection logic block 136. Referring back to the block diagram of FIG. 2, the performance of the motor 88 can be adjusted according to its temperature. The command being passed from the control processor 94 to the motor control circuit 90 may be a function of the motor temperature reading 124. More specifically, the maximum current applied to the motor 88 can be a function of the motor temperature reading 124.

The particulars shown herein are by way of example and for purposes of illustrative discussion of the embodiments of the present disclosure only and are presented in the cause of providing what is believed to be the most useful and readily understood description of the principles and conceptual aspects. In this regard, no attempt is made to show details of the present invention with more particularity than is necessary, the description taken with the drawings making apparent to those skilled in the art how the several forms of the present invention may be embodied in practice.

What is claimed is:

1. A respiratory assistance device, comprising:
   a blower with an output;
   a patient ventilation interface configured for fitment on a patient respiratory passageway, the patient ventilation interface including a ventilation mask and a piloted exhalation valve coupled to the ventilation mask;
   a first conduit coupling the output of the blower to the patient ventilation interface, a pilot line from the first conduit being coupled to the piloted exhalation valve;
   a first pressure sensor for measuring a blower pressure at the output of the blower;
   a second pressure sensor for measuring a mask pressure in the patient ventilation interface; and
   a pressure controller, in communication with the first pressure sensor and the second pressure sensor, that detects a patient inspiratory phase and a patient expiratory phase by comparing a pressure difference ΔP between the blower pressure and the mask pressure to a trigger limit defined as an average of the pressure difference ΔP plus a trigger constant and a cycle limit defined as a maximum of the pressure difference ΔP multiplied by a cycle constant, wherein therapeutic airflow is delivered to the patient during the detected patient inspiratory phase and exhausted through the piloted exhalation valve during the detected patient expiratory phase.

2. The respiratory assistance device of claim 1, wherein the pressure controller actuates the blower to induce the pressure difference ΔP such that the piloted exhalation valve is closed during the patient inspiratory phase and opened during the patient expiratory phase.

3. The respiratory assistance device of claim 2, wherein the piloted exhalation valve is open to ambient pressure with the pressure difference ΔP being lower than a predefined threshold.

4. The respiratory assistance device of claim 2, wherein the piloted exhalation valve is open to ambient pressure with the pressure difference ΔP being approximately zero to negative.

5. The respiratory assistance device of claim 4, wherein the piloted exhalation valve is closed with the pressure difference ΔP being higher relative to the pressure difference ΔP of when the piloted exhalation valve is open.

6. The respiratory assistance device of claim 1, wherein an average of the pressure difference ΔP over one or more patient breathing cycles defines a leak constant.

7. The respiratory assistance device of claim 6, wherein the trigger limit is defined by the leak constant added to the trigger constant.

8. The respiratory assistance device of claim 1, wherein the pressure controller relieves mask pressure by reducing therapeutic airflow delivered to the patient according to a function of the blower pressure.

9. The respiratory assistance device of claim 1, wherein the pressure controller includes a first proportional-integral-derivative (PID) controller and a second proportional-integral-derivative (PID) controller, the first PID controller being part of a first control loop over the blower pressure, and the second PID controller, together within the first control loop, being part of a second control loop for minimizing error between the mask pressure and a set pressure.

10. The respiratory assistance device of claim 1, further comprising:

a temperature sensor for a motor of the blower;
wherein a particular speed at which the motor is driven by the pressure controller to regulate therapeutic airflow is a function of temperature readings from the temperature sensor.

11. The respiratory assistance device of claim 1, further comprising a second conduit, wherein the second pressure sensor is disposed in pneumatic communication with the patient ventilation interface over the second conduit.

12. The respiratory assistance device of claim 11, further comprising a purge solenoid in pneumatic communication with the first conduit and the second conduit and configured to deliver a purge flow to clear the second conduit.

13. A continuous positive airway pressure (CPAP) apparatus for respiratory assistance of a patient, the apparatus comprising:
a blower having an output;
a patient ventilation interface configured for fitment on a respiratory passageway of the patient, the patient ventilation interface including a piloted exhalation valve coupled thereto;
a first conduit coupling the output of the blower to the patient ventilation interface, a pilot line from the first conduit being coupled to the piloted exhalation valve;
a first pressure sensor for measuring a blower pressure at the output of the blower;
a second pressure sensor for measuring a pressure in the patient ventilation interface; and
a pressure controller, in communication with the first pressure sensor and the second pressure sensor, that detects a patient inspiratory phase and a patient expiratory phase by comparing a pressure difference $\Delta P$ between the blower pressure and the mask pressure to a trigger limit defined as an average of the pressure difference $\Delta P$ plus a trigger constant and a cycle limit defined as a maximum of the pressure difference $\Delta P$ multiplied by a cycle constant, wherein therapeutic airflow is delivered to the patient during the detected patient inspiratory phase.

14. The CPAP apparatus of claim 13, wherein the piloted exhalation valve is open to ambient pressure with the pressure difference $\Delta P$ being low lower than a predefined threshold.

15. The CPAP apparatus of claim 13, wherein the piloted exhalation valve is open to ambient pressure with the pressure difference $\Delta P$ being approximately zero to negative.

16. The CPAP apparatus of claim 13, wherein the piloted exhalation valve is closed with the pressure difference $\Delta P$ being higher relative to a pressure difference $\Delta P$ of when the piloted exhalation valve is open.

17. The CPAP apparatus of claim 13, further comprising:
a temperature sensor for a motor of the blower;
wherein a particular speed at which the motor is driven by the pressure controller to regulate the therapeutic airflow is a function of temperature readings from the temperature sensor.

18. A method for administering continuous positive airway pressure (CPAP) therapy to a patient, the method comprising:

receiving a first CPAP therapeutic pressure value;
measuring a blower pressure value at an output of a blower generating therapeutic gas flow through a first conduit to a ventilation mask wearable by the patient, the ventilation mask including a piloted exhalation valve;
measuring a mask pressure value at the ventilation mask;
generating a pressure difference value $\Delta P$ between the blower pressure value and the mask pressure value;
evaluating a patient respiratory state by comparing the pressure difference value $\Delta P$ to a trigger limit value defined as an average of the pressure difference $\Delta P$ plus a trigger constant and a cycle limit value defined as a maximum of the pressure difference $\Delta P$ multiplied by a cycle constant, the patient respiratory state being one of an inspiration state and an expiration state; and
selectively applying a quantity of the therapeutic gas flow through the first conduit to the ventilation mask in response to the evaluated patient respiratory state, the quantity of therapeutic gas flow generated by the blower corresponding to the first CPAP therapeutic pressure value.

19. The method of claim 18, wherein the selectively applied quantity of the therapeutic gas flow to the patient induces a pressure differential between the output of the blower and the ventilation mask, and wherein the piloted exhalation valve is opened and closed in response to the induced pressure differential.

20. The method of claim 18, further comprising:
measuring an operating speed of the blower;
measuring an operating temperature of the blower; and
modulating the quantity of the therapeutic gas flow generated by the blower as a function of the operating speed and the operating temperature of the blower.

21. The method of claim 18, further comprising:
generating a leak constant value from an average of the pressure difference $\Delta P$ over a predetermined time period.

22. The method of claim 21, further comprising:
generating the trigger limit value based upon the leak constant value summed with the trigger constant; and
triggering the blower based upon the pressure difference $\Delta P$ reaching the trigger limit value;
wherein the selectively applying the quantity of the therapeutic gas flow through the first conduit to the ventilation mask corresponds to the triggering the blower.

23. The method of claim 21, further comprising:
generating the cycle limit value based upon a cycle constant fraction of a maximum of the pressure difference $\Delta P$; and
cycling the blower based upon the pressure difference $\Delta P$ reaching the cycle limit value;
wherein the selectively applying the quantity of therapeutic gas flow through the first conduit to the ventilation mask corresponds to the cycling the blower.

* * * * *